United States Patent [19]

Makiej, Jr.

[11] Patent Number: 5,664,557
[45] Date of Patent: Sep. 9, 1997

[54] RELEASABLY ENGAGEABLE COUPLING FOR AN INHALER

[75] Inventor: Walter J. Makiej, Jr., Chelmsford, Mass.

[73] Assignee: Respiratory Delivery Systems, Inc., Chelmsford, Mass.

[21] Appl. No.: 579,382

[22] Filed: Dec. 27, 1995

Related U.S. Application Data

[63] Continuation-in-part of Ser. No. 209,199, Mar. 10, 1994, abandoned.

[51] Int. Cl.$^6$ ............................................ A61M 11/00
[52] U.S. Cl. ........................ 128/200.23; 128/203.12; 222/135
[58] Field of Search ............... 128/200.19, 200.14, 128/200.23, 203.12, 203.22, 203.27, 204.13, 205.21; 222/135, 402.24; 131/179

[56] References Cited

U.S. PATENT DOCUMENTS

| | | | |
|---|---|---|---|
| 3,269,389 | 8/1966 | Meurer et al. | 128/200.14 |
| 3,704,725 | 12/1972 | Marand | 222/402.24 |
| 4,040,420 | 8/1977 | Speer | 222/135 |
| 4,261,481 | 4/1981 | Speer | 222/135 |
| 4,463,754 | 8/1984 | McDonald | 128/200.19 |
| 4,627,432 | 12/1986 | Newell et al. | 128/200.19 |
| 4,694,824 | 9/1987 | Ruderian | 128/200.19 |
| 4,887,591 | 12/1989 | Okumura | 128/205.21 |
| 4,953,547 | 9/1990 | Poole | 128/203.12 |
| 5,002,048 | 3/1991 | Makiej | 128/200.23 |
| 5,020,527 | 6/1991 | Dessertine | 128/200.23 |

FOREIGN PATENT DOCUMENTS

| | | | |
|---|---|---|---|
| 9217231 | 10/1992 | WIPO | 128/200.14 |
| 9409842 | 5/1994 | WIPO | 128/203.12 |

*Primary Examiner*—V. Millin
*Assistant Examiner*—William J. Deane, Jr.
*Attorney, Agent, or Firm*—Wolf, Greenfield & Sacks P.C.

[57] ABSTRACT

A releasably engageable inhaler including a housing for holding medicine to be delivered to a patient through a discharge port. A connector allows the selective engagement of the inhaler to other inhalers which may contain the same or a different medication. An indicator on the surface of the housing allows the patient to distinguish the contents of the inhaler or the sequence in which the medicine in two or more engaged inhalers should be taken.

14 Claims, 7 Drawing Sheets

RELEASABLY ENGAGEABLE COUPLING FOR AN INHALER

CROSS REFERENCE TO RELATED APPLICATION

This application is a continuation in part of application Ser. No. 08/209,199, filed Mar. 10, 1994, now abandoned.

BACKGROUND OF THE INVENTION

1. Field of the Invention

The present invention relates to a releasably engageable coupling for an inhaler that administers medicine to a patient through the nose or mouth.

2. Description of the Related Art

Numerous devices are known for administering medicine to a patient's nasal membranes, trachea or bronchial passages. Such devices are commonly referred to as inhalers.

The inhaler 1 illustrated in FIG. 1, employs a metered-dose, pressurized, aerosol canister 2 which is inserted in an opening 3 in the inhaler housing 4, and is typically known as an MDI (metered-dose inhaler). An aerosol medicinal spray is discharged through a mouthpiece 5 (or nasalpiece) into the airway of the patient. Numerous variations of this basic configuration are known, including those having mechanical features for improving the coordination between a patient's release of medication and the patient's inhalation thereof. It also is known to employ a spacer device, generally attached to the mouthpiece or nasalpiece, to facilitate the acceptance and delivery of the medication.

Also known are dry powder inhalers. A representative single dose inhaler 6, shown in FIGS. 2A-B, has a discharge port 7 and a receiving section 8 for holding a dry powder capsule. A blade within the inhaler (not shown) breaks open an inserted capsule when the port and receiving section are rotated relative to each other. The powder deposited in the interior of the inhaler is then sucked through the discharge port 7, along with air which enters the inhaler through vent 10.

Certain patient therapies involve two or more different medicines. For example, asthmatics commonly use a "beta 2" drag to first open up the bronchial passageways, followed by asteroid to reduce inflammation. The proper sequence and co-action of the drugs is important for enhancing therapeutic efficiency. Currently, such drugs are administered by two separate inhalers. As a result, patients may lose or forget to use one of the medications or may take the medications in the wrong sequence. Another problem with conventional inhalers is that it is difficult for a patient to know when the container holding the medication approaches empty. Particularly for patients with chronic or acute illness, the failure to have a spare inhaler can lead to severe consequences.

Meuer, et at., U.S. Pat. No. 3,269,389 disclose a compartmental dispensing container for nose and throat preparations. The dispensing container provides a single flexible resilient unit container that holds two non-compatible products in separate compartments until they are simultaneously dispensed from the container through immediately adjacent ports.

There also has been proposed in applicant's U.S. Pat. No. 5,002,048 and in U.S. Pat. No. 5,007,419 to provide a single inhaler housing adapted to receive and discharge two different medications. This device is complex to manufacture and may require FDA approval. Consequently, the prior art still lacks an easily fabricated inhaler which is selectively and releasably engageable to one or more other inhalers and which will not require FDA approval.

SUMMARY OF THE INVENTION

The present invention provides an inhaler which is releasably engageable to at least one other inhaler. The inhaler includes a housing adapted to receive a medication, preferably in aerosol or powder form, and a port through which the medicine is discharged into the patient's nose or mouth. The inhaler may be releasably engaged to at least one other inhaler, by a connector which engages the upstanding portion of the inhaler housing. In various aspects of the invention, suitable connectors may include a male/female locking arrangement, a hook and loop fastening material, such as a product sold under the tradename VELCRO, an adhesive strip and a cap which is adapted to receive portions of the inhaler housing in a tight fitting relationship. The inhaler housing may be provided with visible indicators or indicators discernible by touch to permit the patient to distinguish the medicines delivered by the inhaler, ensuring that a desired therapeutic sequence is followed.

The releasably engageable feature of the inhaler facilitates variation in medicinal therapy. A first inhaler may be connected to a second inhaler to provide a first sequence of treatment. Where a second therapy is prescribed, the first inhaler is detached from the second inhaler and joined to a third inhaler. Alternatively, where a three dose treatment is required, the original first and second inhaler assembly may be joined to the third inhaler. The releasably engageable nature of the inhaler allows such versatility, while minimizing the overall cost of treatment to the patient.

Another embodiment of the invention provides a connector which is designed to hold together two or more inhaler housings. The connector may include two C-shaped clips that clench against, and retain, the inhaler housings. Alternatively, a single C-shaped clip may be molded to, or mounted, on the housing of an inhaler. The clips, according to this embodiment, are constructed to releasably engage an associated inhaler. The connector may be made from a material which is, or is constructed to be, springy so that the inhalers may be resiliently secured by the C-shaped clips. Alternatively, the inhalers may be retained in a closely fitting, such as a frictional fit, but not necessarily resilient, connecting clip.

Other aspects of the present invention will become apparent to those skilled in the art, upon reading the following description of various embodiments of the present invention.

BRIEF DESCRIPTION OF THE DRAWING

Like reference numerals indicate like elements in the Figures, in which.

DETAILED DESCRIPTION

The present invention will be better understood in view of the following description, read in connection with the Figures.

Figure 1:
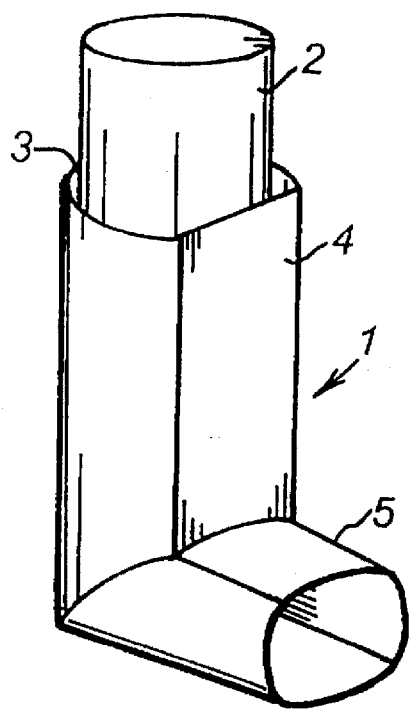
FIG. 1 shows a conventional metered dose oral inhaler.
Figure 2A:
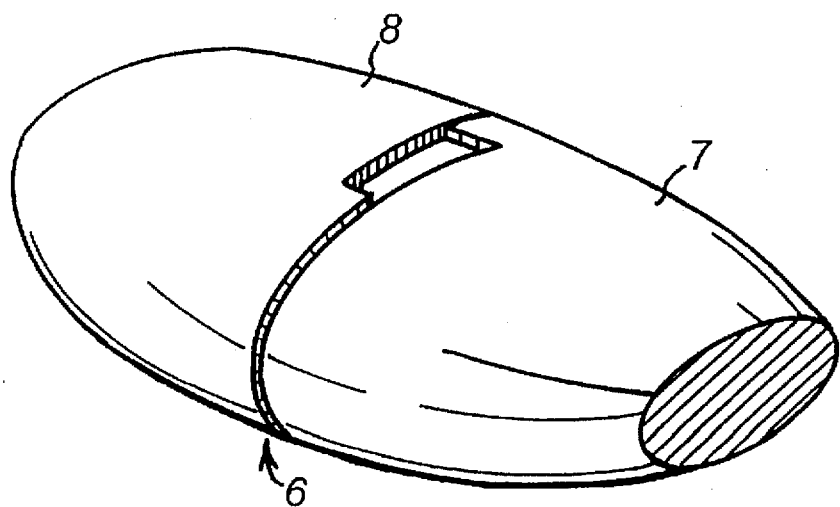
FIG. 2A is a general view of a capsule fed oral inhaler.
Figure 2B:
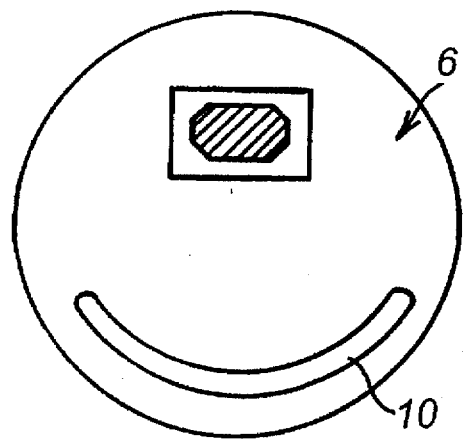
FIG. 2B is a view of the back of the inhaler of FIG. 2A.
Figure 3A:
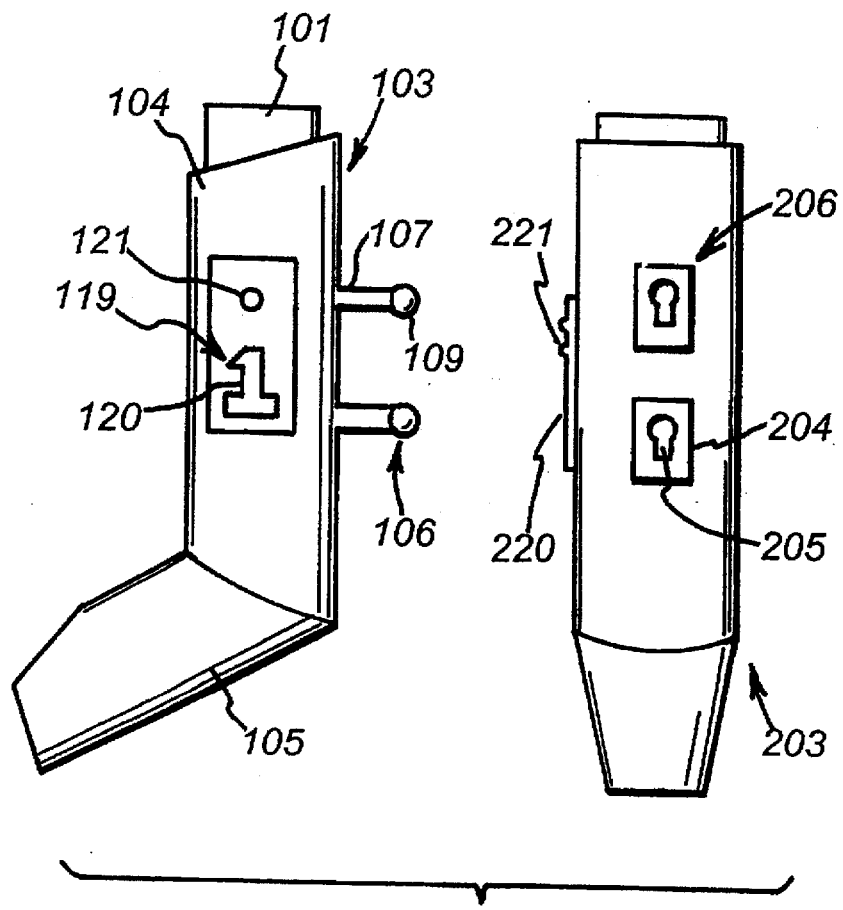
FIGS. 3A–3B illustrate one embodiment of an inhaler in accordance with the present invention.
Figure 3B:
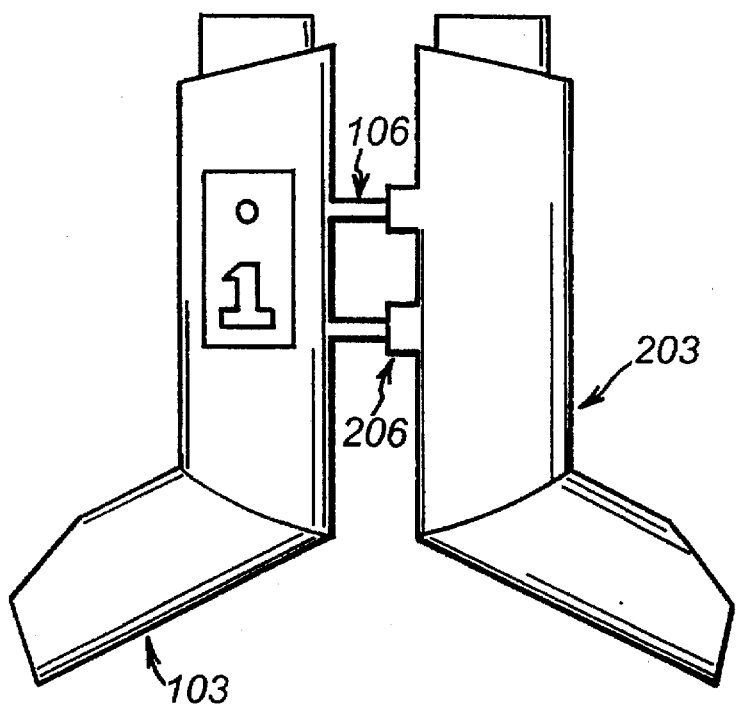

FIGS. 3A–3B illustrate a releasably engageable inhaler 103 for use with an aerosol dischargeable medication that includes a housing 104 having a first portion adapted to receive a pressurized container of medicine 101, a valve (not shown) into which the outlet tube of the container is inserted, and a port 105 through which the medicinal spray is discharged from the housing into the nose or mouth of the patient.

Inhaler 103 includes a connector 106 for releasably engaging a compatible connector 206 in inhaler 203. The connector may be either a male or female component. In the embodiment shown, the male part includes a shaft 107 having a ball 109 at the end thereof. The female part 204 includes a keyhole slot 205 for receiving the ball 109 and locking the two inhalers 103 and 203 together, as shown in FIG. 3B. Other male/female locking configurations are contemplated, such as a bayonet and sheath arrangement. It should be understood that the male part and the female part could be located in other suitable locations on the inhaler housing, for example on a sideward portion with respect to the discharge port. Further, the locking members need not be disposed in the same position on the respective inhalers. The male part could project from the back of the inhaler, as shown, while the female engagement could be positioned on a sidewall portion of the housing. Moreover, while a specific male/female configuration is shown, the invention is not limited to such an arrangement and contemplates other detachable locking mechanisms as would be apparent to those of skill in the art. Where more than two inhalers are to be releasably engaged, at least one of the inhaler housings should be provided with two or more connectors.

An indicator 119 may be provided on the inhaler housing to identify its medicinal contents or the sequence in which the medications should be taken when the inhaler is releasably engaged to another inhaler. The indicator may be discernible visually, by touch, or by a combination thereof. In the assembly illustrated in FIGS. 3A–3B, there is printed, embossed, or otherwise visually indicated a sequence number 120, for informing the patient which medicine to take first and a sequence number 220 informing the patient which medicine to take second. Raised bumps 121 and 221, also are provided, and are tactilely discernible. A combined visual and tactile discernible indicator may be provided by molding raised numbers into the inhaler housing. Other suitable indicators will be readily apparent to those skilled in the art. In those situations where inhalers with different medications are intended to be engaged, the locking members may be configured so that only inhalers with different indicators are engageable. Thus, inhalers with like indicators will each have, for example, only male locking members which preclude the unintended engagement of inhalers containing the same medication.

Figure 4:
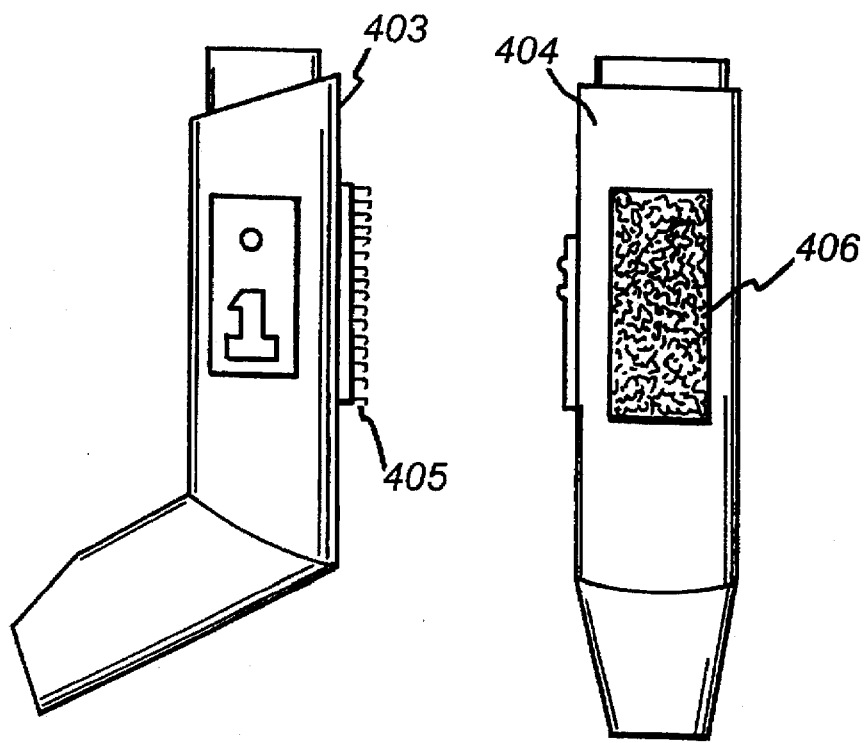
FIG. 4 is a view of another embodiment of an inhaler according to the present invention.

FIG. 4 illustrates another embodiment of the invention in which the inhaler housings 403 and 404 are releasably connected through a hook 405 and loop 406 connector. One example of such an arrangement is VELCRO™ brand fastening tape. In this embodiment, the hook and loop connector enables the inhaler housings to be connected with minimal contact force. The hook and loop fasteners also provide for a secure attachment of the two inhaler housings.

Figure 5:
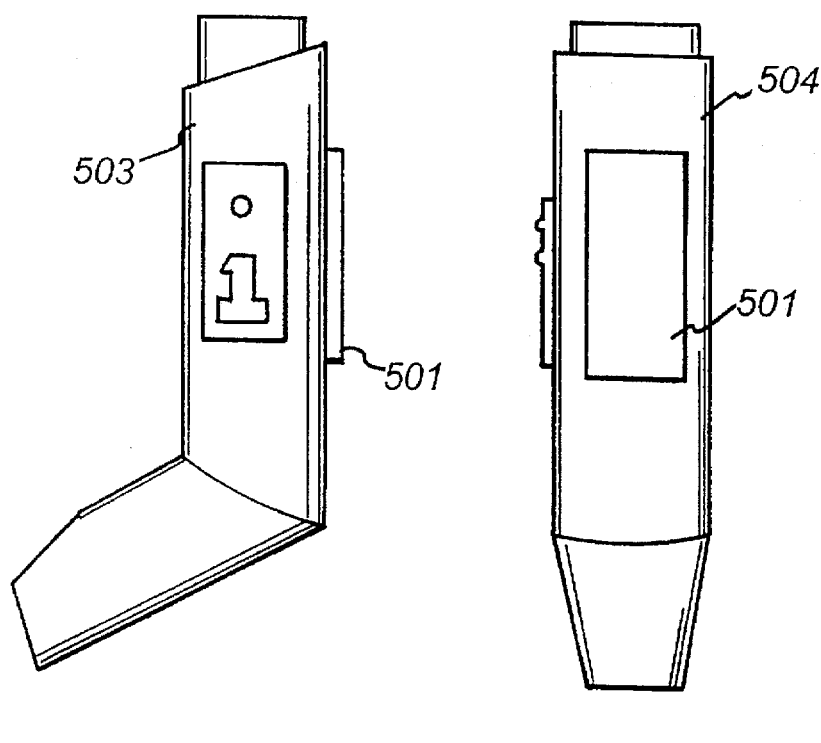
FIG. 5 is a view of yet another embodiment of the present invention.

Yet another embodiment of the present invention is illustrated in FIG. 5, wherein the connector includes a releasable adhesive covered strip 501 which joins inhaler housing 503 to inhaler housing 504. An adhesive strip may be provided on one or both of the inhalers.

Figure 6:
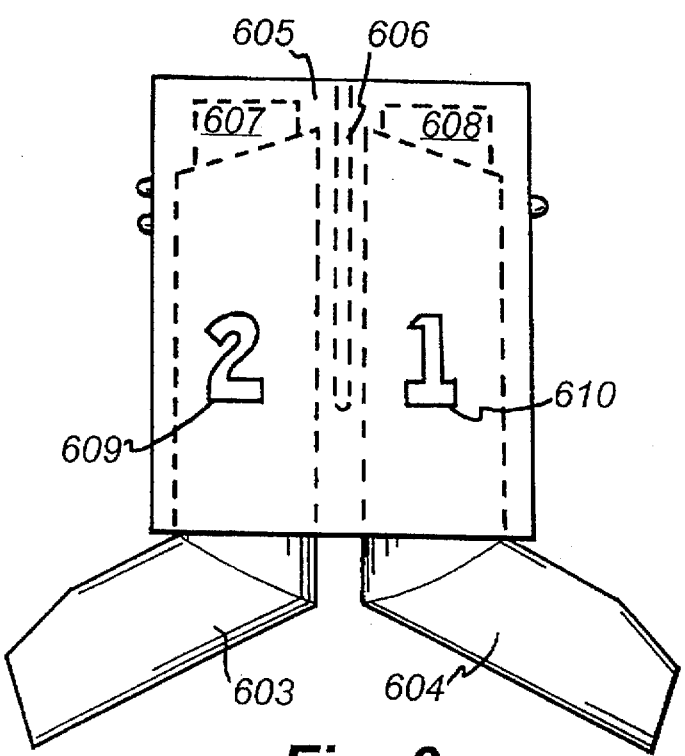
FIG. 6 is a view of yet another embodiment of an inhaler according to the present invention.

FIG. 6 illustrates another embodiment of the present invention is in which inhaler housing 603 is joined to housing 604 by a cap 605 into which the inhaler housings are received in a tight fitting relationship. The cap may be molded to have an interior which conforms to the shape of the received portion of the inhaler and may include a dividing wall 606. A further locking mechanism may be provided to enhance the engagement of the cap and inhalers. For example, a rail could be provided along the surface of the inhaler which is slidably received in a compatible locking sheath in the inner surface of the cap. Other arrangements would be apparent to those of skill in the art. The cap 605 may be of a length such that canisters 607 or 608 may be actuated by pressing on the bottom of inhaler housing, even while the inhaler is engaged in the cap. Alternatively, the cap may be provided with an opening through which the actuating end of the containers project and are accessible to manual depression by the user. Furthermore, the cap may include indicators 609 and 610, similar to the indicators described above.

Figure 7:
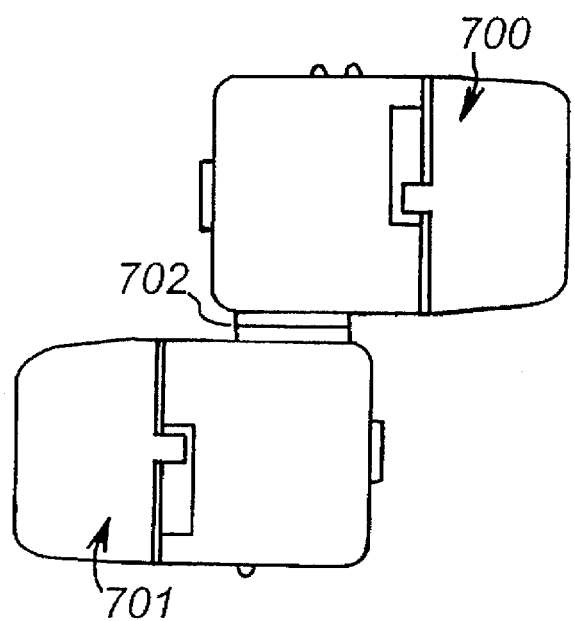
FIG. 7 is a view of yet another embodiment of an inhaler according to the present invention.
Figure 8:
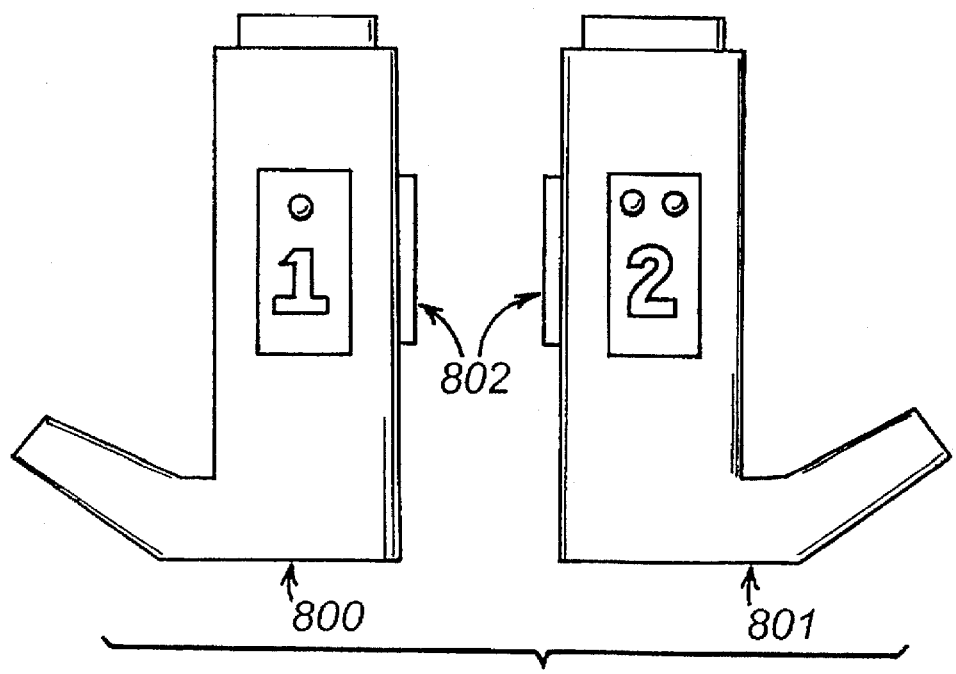
FIG. 8 is a view of yet another embodiment of an inhaler according to the present invention.

The principles described above in connection with the specific embodiments related to oral aerosol inhalers may also be applied to dry powder inhalers and nasal inhalers, as shown in FIGS. 7 and 8. In accordance with the embodiment shown in FIG. 7, there is provided dry powder inhalers 700 and 701 which are releasably engaged by a connector 702 which includes any of the means described above in connection with FIGS. 3A–5. In the embodiment of FIG. 8, an assembly of nasal inhalers 800 and 801 is shown, which includes a connector arrangement 802, which may be any of the means described and illustrated in connection with FIGS. 3A–5.

Figure 9:
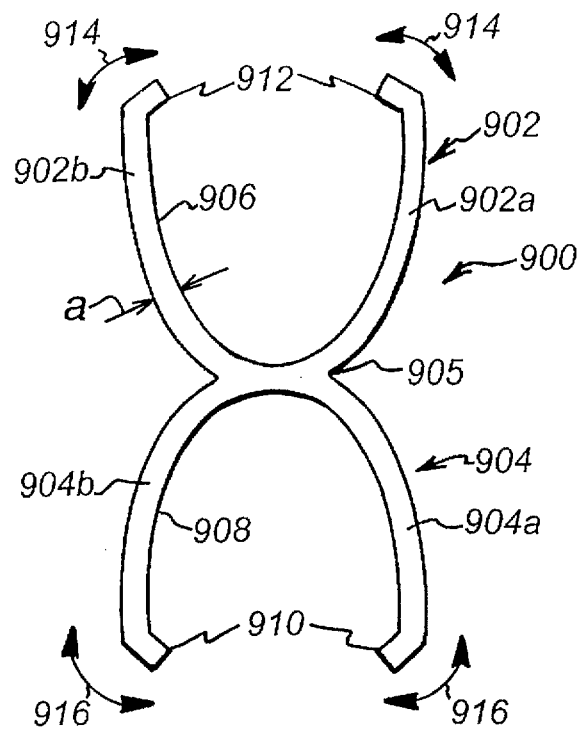
FIG. 9 is a top view of another embodiment of an inhaler connector according to the present invention taken along sectional line 9—9 in FIG. 10.
Figure 10:
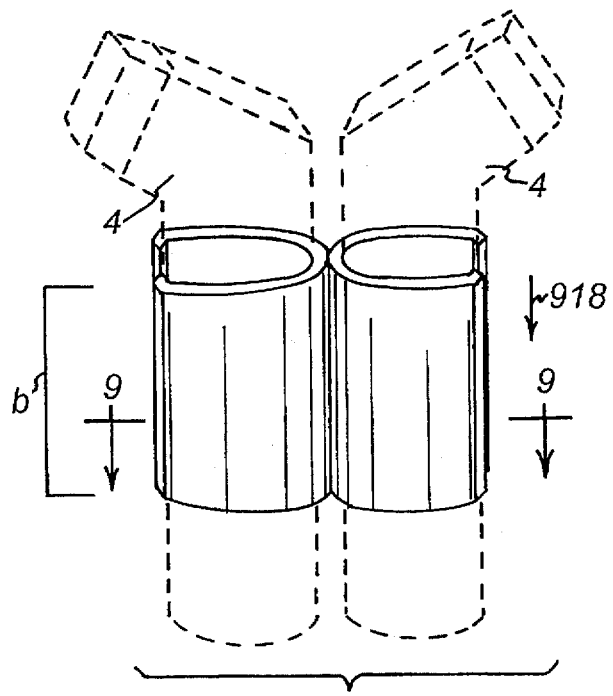
FIG. 10 is a perspective side view of the embodiment illustrated in FIG. 9, showing the inhalers in phantom lines; and, FIG. 11 is another embodiment of the invention illustrating a connector mounted to an inhaler housing, an inhaler housing is shown in phantom in the clip.

In another embodiment of the releasably engageable coupling for an inhaler, shown in FIGS. 9 and 10, a connector, indicated generally by 900, is provided with two C-shaped clips 902 and 904 attached at a common back wall 905. FIG. 9 illustrates a transverse cross-section taken from sectional line 9—9 in FIG. 10. The clip 902 has arms 902a and 902b which curve in a C-shape. Similarly, clip 904 has arms 904a and 904b. The arms of each clip form an opening that is constructed and arranged to hold an inhaler housing 4, shown in phantom in FIG. 10. As shown, each inhaler is oriented in an upright position. Alternatively, one inhaler may be inverted.

The connector 900 may orient the inhaler ports in opposite directions, as shown. Alternatively, the connector may be configured to orient the ports in the same direction or such that the ports are oriented at an angle relative to one another. When the connector is configured to orient the ports in the same direction, the clips of the connector may be arranged side-by-side. One skilled in the art will recognize that various configurations are possible for the clip. While disclosed as C-shaped, the connector configuration may take any form necessary to releasably clip the housing and, therefore, is dependent upon the shape of the housing portion to which it is attached.

The connector 900 may be made from a material which is, or constructed in a configuration so as to be, springy such that the inhaler 4 can be resiliently held by clips 902, 904. In this arrangement, the inhaler ports may be reoriented by rotating or mining the housing within the coupler clip. Although many different plastics will be recognized as suitable, polypropylene material may be particularly appropriate. Of course, other acceptable materials will be recognized by those of ordinary skill in the art. The connector may be formed of one piece of material or, alternatively, two C-shaped clips may be attached to each other.

The ends of arms of the clips 902 and 904 may have inwardly directed extensions 910 and 912. These extensions may further secure the inhaler within the surface 906 and 908 of the clip. Because the clip may be made of a springy material, the arms 902 and 904 can move in the direction indicated by arrows 914 and 916 shown in FIG. 9. Additionally, the inhalers 4 may be inserted through the openings in the clip, as indicated by arrow 918, and held in place where the dimension of the opening closely fits the shape of the inhaler. Alternatively, the clip and inhaler may included compatible locking structures such as described in connection with the other embodiments disclosed herein or other arrangements as would be apparent to one of skill in the art.

In a preferred embodiment of the invention, the connector 900 has a thickness "a" indicated in FIG. 9, which may be between about 0.05 inches and about 0.010 inches. In a presently preferred embodiment two desired thicknesses are 0.063 and 0.093 inches. Of course, greater and lesser thicknesses are contemplated. One skilled in the art will recognize that various thicknesses are acceptable. Also in a presently preferred embodiment, the length of the connector "b" as indicated in FIG. 10, may be about 1 inch. The length b should be chosen which is sufficient to secure the inhalers within the C-shape and that will provide for convenient and reliable use.

Figure 11:
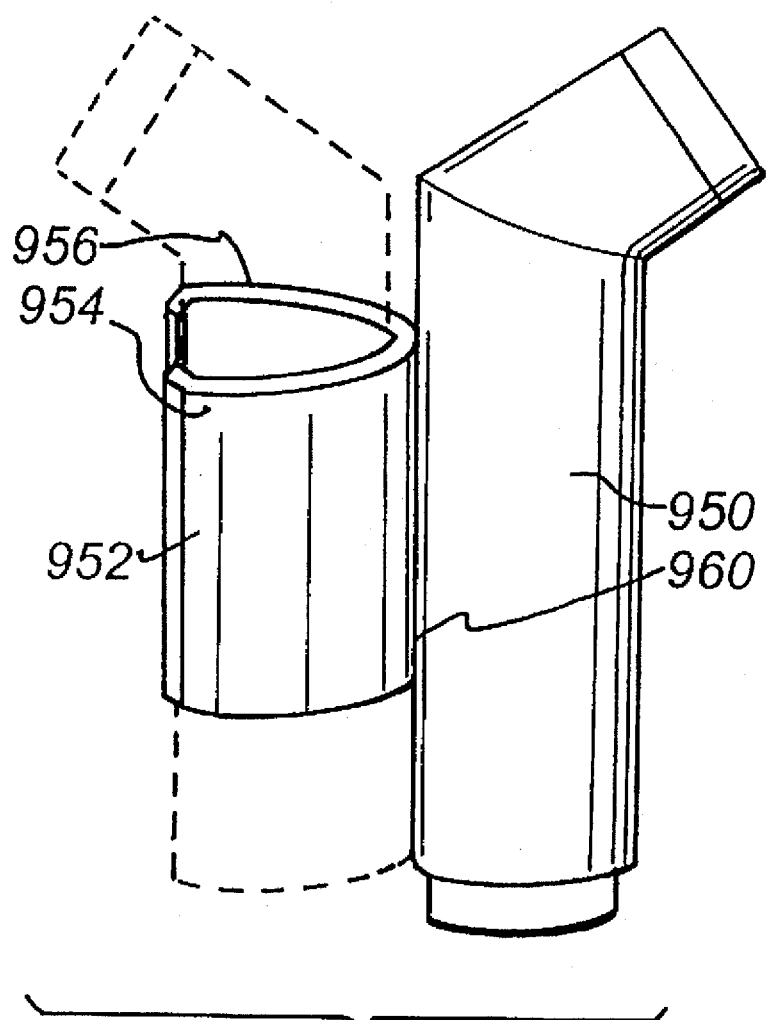

FIG. 11 shows an alternate embodiment of the releasably engageable connector. In this embodiment, an inhaler housing 950 includes a C-shaped clip 952 mounted on the side of the inhaler housing. The clip 952 includes two arms 954 and 956, similar to the previously described clip. Additionally, extensions are provided to secure the inhaler 4, shown in phantom. As in the prior described embodiment, the clip may be made of a springy material so that the inhaler may be secured to the clip through the C-shaped clip opening. Alternatively, the inhaler may be inserted on the clip by the top or bottom opening.

The clip 952 may be molded with the inhaler housing 950 along a side surface 960. Alternatively, it may be mounted to the inhaler housing with, for example, glue or other adhesive material. The clip may be made of the same, or a different, material as the inhaler housing 950.

In each of the embodiments described in FIGS. 9–11, the releasably engageable inhaler provides a holding clip or a clamp for currently approved MDI products. The releasably engageable inhaler provides a convenience benefit that greatly increases the likelihood of patient compliance with therapeutic indications. When a patient is fully compliant, the full therapeutic benefits of a medicinal treatment may be obtained.

The connector of the present invention secures two or more inhalers together. The inhalers may have the same medication, where one of the medication containers is a spare. Additionally, and importantly, often medicines, such as asthma drags, must be taken serially so that the proper therapeutic benefits of the drag may be delivered. For example, often an asthma patient must first inhale a "beta 2" drug to open up the airways and then inhale asteroid drag to reduce intimation. The clip may be used to provide a simple and convenient way to keep the two medications together. When the drags are taken serially as indicated, the optimal therapeutic benefits are achieved. As indicated above, a visually or tacitly discernible reference character may be placed on the inhalers as a reminder which to take first.

Many asthmatic patients are on at least two inhaler medications and the clip provides a convenient way of carrying and keeping the aerosol medications together. As shown, two aerosol inhalers may be connected with the clip. One skilled in the art will recognize that more than two inhalers may be clipped together using a clip having a different configuration. For example, when three or more inhalers are clipped together, the clip may take on a star or square configuration.

The present invention has now been described in connection with a number of specific embodiments thereof. However, numerous modifications which are contemplated as falling within the scope of the present invention should now be apparent to those skilled in the art. Therefore, it is intended that the scope of the present invention be limited only by the scope of the claims appended hereto.

What is claimed is:

1. In combination, an inhaler coupler and at least two completely functionally separate and independent metered dose inhalers engaged to said inhaler coupler wherein each of said at least two metered dose inhalers includes an elongated housing having a chamber in which is received a container of pressurized medication and a port through which said medication is discharged from said container in a metered dose to the patient and wherein said inhaler coupler includes a connector that is releasably engaged to one or more of said at least two inhaler housings, said combination allowing separate and non-simultaneous administration of medication from any of said at least two independent metered dose inhalers.

2. The combination of claim 1, wherein said connector includes one or more clips that are constructed and arranged to releasably receive and retain one or more of said at least two inhaler housings.

3. The combination recited in claim 2, wherein said one or more clips are C-shaped.

4. The combination recited in claim 1 wherein said connector resiliently engages one or more of said at least two inhaler housings.

5. The combination recited in claim 3, wherein said at least one or more one C-shaped clips further includes inwardly directed extensions thereof.

6. The combination recited in claim 1 wherein said connector includes two clips joined at a common back wall.

7. The combination recited in claim 1, further comprising an indicator disposed on one or more of said at least two inhaler housings for distinguishing said medication contained in said at least two functional and completely independent metered dose inhalers.

8. The combination recited in claim 1 wherein said ports of said at least two inhaler housings extend in diverging directions.

9. The combination recited in claim 1 wherein said ports of said at least two inhaler housings extend in diametrically opposite directions.

10. The combination recited in claim 1 wherein each of said at least two inhaler housings is rotatable within said connector.

11. The combination recited in claim 1 wherein said connector includes one or more clips which define a respective opening that is constructed and arranged to closely match the shape of, and in which is engageably received, one of said at least two inhaler housings.

12. The combination recited in claim 2 wherein said one or more clips resiliently engage said at least two inhaler housings.

13. The combination recited in claim 1 wherein said elongated housing includes an L-shape having a transverse portion including said port and an upstanding portion that defines said chamber and in which is received said container of pressurized medication, wherein said connector engages said upstanding portion of one or more of said at least two inhaler housings.

14. The combination recited in claim 1 wherein said housing is rigid and non-squeezable.

* * * * *